United States Patent [19]

Kahn et al.

[11] Patent Number: 5,208,385

[45] Date of Patent: May 4, 1993

[54] PREPARATION OF TETRAHYDROFURAN POLYMERS HAVING A NARROW MOLECULAR WEIGHT DISTRIBUTION USING AN AMORPHOUS SILICA-ALUMINA CATALYST

[75] Inventors: Andrew P. Kahn, Wayne; Robert G. Gastinger; Rangasamy Pitchai, both of West Chester, all of Pa.

[73] Assignee: Arco Chemical Technology, L.P., Wilmington, Del.

[21] Appl. No.: 839,538

[22] Filed: Feb. 19, 1992

[51] Int. Cl.$^5$ .................. C07C 41/01; C07C 41/02
[52] U.S. Cl. ........................ 568/617; 560/240
[58] Field of Search .................. 568/617; 560/240

[56] References Cited

U.S. PATENT DOCUMENTS

| | | | |
|---|---|---|---|
| 3,433,829 | 3/1969 | Dorfelt | 260/496 |
| 4,189,566 | 2/1980 | Mueller et al. | 528/408 |
| 4,230,892 | 10/1980 | Prockmayr | 568/617 |
| 4,243,799 | 1/1981 | Mueller et al. | 528/409 |
| 4,303,782 | 12/1981 | McHale et al. | 528/416 |
| 4,363,924 | 12/1982 | Mueller et al. | 549/509 |
| 4,510,333 | 4/1985 | Pruckmayr | 568/617 |
| 4,670,519 | 6/1987 | Mueller | 525/342 |
| 4,728,722 | 3/1988 | Mueller | 528/413 |
| 4,762,951 | 8/1988 | Mueller | 568/617 |
| 4,933,503 | 6/1990 | Mueller | 568/621 |
| 5,053,553 | 10/1991 | Dorai | 568/617 |

*Primary Examiner*—Howard T. Mars
*Attorney, Agent, or Firm*—Jonathan L. Schuchardt

[57] ABSTRACT

A process for producing tetrahydrofuran polymers having a narrow molecular weight distribution is disclosed. Tetrahydrofuran is polymerized in the presence of a carboxylic acid anhydride and amorphous silica-alumina. The process overcomes the need for costly post-treatment techniques such as distillation and selective solvent extraction.

7 Claims, No Drawings

PREPARATION OF TETRAHYDROFURAN POLYMERS HAVING A NARROW MOLECULAR WEIGHT DISTRIBUTION USING AN AMORPHOUS SILICA-ALUMINA CATALYST

FIELD OF THE INVENTION

The invention relates to the synthesis of tetrahydrofuran polymers (poly(THF)). A process for preparing polytetrahydrofuran having a narrow molecular weight distribution is revealed. The polymers are especially valuable for the manufacture of polyurethanes and thermoplastic polyesters having superior mechanical properties.

BACKGROUND OF THE INVENTION

Polytetramethylene ether glycols, which are useful soft segments for applications such as polyurethane elastomers and thermoplastic polyesters, are produced by polymerizing tetrahydrofuran in the presence of a cationic initiator. Commercially important cationic initiators include strong, soluble acids such as fuming sulfuric acid and fluorosulfonic acid. Polytetrahydrofuran diols produced using the soluble acid initiators have a sufficiently narrow molecular weight distribution ($M_w/M_n$ less than about 3) for many applications. Unfortunately, these processes generate large amounts of acidic wastes that require costly treatment and disposal. In addition, product consistency is difficult to achieve because the polymerizations are highly exothermic, and satisfactory product consistency requires careful control of reaction temperature.

Many of the problems of the soluble acid catalysts are avoided by using a "bleaching earth" catalyst (see, for example, U.S. Pat. Nos. 3,433,829, 4,189,566, and 4,243,799). The bleaching earths known in the art include naturally occurring aluminum hydrosilicates and aluminum/magnesium hydrosilicates of the montmorillonite type. The clays are normally activated by acid washing. A carboxylic acid anhydride is used as an activator, and the resulting polytetramethylene ether polymer has ester end groups. The ester end groups can be converted to hydroxyl end groups by base-catalyzed transesterification with an alcohol (see U.S. Pat. No. 4,230,892) or by catalytic hydrogenation.

A key disadvantage of the bleaching earth catalysts is that the polymers produced have higher polydispersities ($M_w/M_n$) than desirable, typically 3–4 at molecular weights of about 400 to 3000. It is well known in the art that the molecular weight distribution (MWD) of the poly(THF) impacts the properties of the polyurethanes or polyesters made therefrom. In general, mechanical properties of finished products are superior when poly(THF) having a relatively narrow molecular weight distribution is used (see U.S. Pat. No. 4,933,503, column 2).

There are two general approaches to obtaining poly(THF) having a relatively narrow MWD. In one approach, poly(THF) having a broad MWD is prepared, and the product is post-treated either by distillation to separate low molecular weight oligomers, selective depolymerization (see, for example, U.S. Pat. No 4,363,924), selective solvent extraction with water/alcohol/hydrocarbon systems (see U.S. Pat. No. 4,762,951), or a combination of these techniques (see U.S. Pat. No. 4,933,503). All of these post-polymerization techniques are expensive, labor-intensive, and time consuming. The object of the second general approach is to eliminate the need for post-treatment by preparing poly(THF) having a narrow MWD. In one method, a low concentration of an alkylene oxide must be maintained throughout the THF polymerization (U.S. Pat. No. 4,728,722). In another method, the mole ratio of the reactants and reaction temperature must be carefully controlled (U.S. Pat. No. 4,510,333).

A solid acid catalyst with the advantages of the bleaching earth catalysts, yet one that inherently gives polymers having a narrower molecular weight distribution than what is possible with the bleaching earths (and therefore overcomes the need for post-treatment), is needed.

SUMMARY OF THE INVENTION

The invention is a process for producing a tetrahydrofuran polymer having a narrow molecular weight distribution. The process comprises polymerizing tetrahydrofuran in the presence of a carboxylic acid anhydride and an amorphous silica-alumina catalyst. Other cationically polymerizable monomers, such as epoxides and oxetanes, may be included to give copolymers with tetrahydrofuran. The process of the invention eliminates the need for costly post-treatment procedures such as distillation and/or selective solvent extraction.

DETAILED DESCRIPTION OF THE INVENTION

In the process of the invention, a tetrahydrofuran polymer having a relatively narrow molecular weight distribution is produced by polymerizing THF and optionally other monomers in the presence of a carboxylic acid anhydride and an amorphous silica-alumina catalyst.

Any grade of tetrahydrofuran can be used in the process of the invention. Optionally, one or more additional cationically polymerizable monomers can also be included. Suitable copolymerizable monomers include epoxides such as ethylene oxide and propylene oxide, oxetanes, substituted oxolanes such as 3-methyltetrahydrofuran, and the like, and mixtures thereof. Preferred comonomers are ethylene oxide and propylene oxide.

A carboxylic acid anhydride is used as an activator. Suitable carboxylic acid anhydrides include acetic anhydride, propionic anhydride, phthalic anhydride, maleic anhydride, and the like. Acetic anhydride is preferred.

The amount of carboxylic acid anhydride used is not critical, but the ratio of tetrahydrofuran to anhydride affects the molecular weight of the polymer obtained. Generally, it is preferred that the mole ratio of tetrahydrofuran to carboxylic acid anhydride be within the range of about 1 to about 50. A more preferred range is from about 10 to about 30. In general, the higher the mole ratio of THF to anhydride, the higher the molecular weight of the resulting polymer.

The catalysts useful in the invention are amorphous silica-aluminas. These catalysts typically contain from about 10 to about 30 weight percent alumina and have surface areas within the range of about 20–500 $m^2/g$. Suitable catalysts are available from Davison/Grace (grades 970-13, 979, 980-13, 980-25, 135, MS13/110). Any form of the catalyst, e.g., powder, granule, pellet, etc., is suitable. These synthetic, amorphous materials can be prepared from hydrolyzable mixtures of silicon and aluminum compounds.

The amorphous silica-aluminas used in the invention should not be confused with zeolites or the naturally occurring montmorillonite clays already known in the art for THF polymerization. The montmorillonites are crystalline and have a characteristic layered, sheet-like structure; zeolites have a crystalline, cage-like, channeled structure. Montmorillonites can be used to prepare tetrahydrofuran polymers, but the molecular weight distributions obtained are higher than desirable. Zeolites such as ZSM-5 give poly(THF)s with molecular weights in the 250,000 to 500,000 range (U.S. Pat. No. 4,303,782).

In contrast, the poly(THF) products from the process of the invention have molecular weights that make them useful intermediates for polyurethane applications. Typically, the molecular weights obtained will be within the range of about 200 to about 5000, preferably from about 250 to about 2000 and a molecular weight distribution ($M_w/M_m$) less than about 3.

The process of the invention can be performed at any desired temperature. Especially suitable is a temperature range from about 20° C. to about 70° C. A more preferred range is from about 40° C. to about 60° C.

The process of the invention can be performed at pressures less than, greater than, or equal to atmospheric pressure, although it is typically most convenient to perform the process at atmospheric pressure.

The process of the invention can be performed batchwise, semi-batchwise, or continuously, as desired.

An inert organic solvent can be employed if desired. Suitable organic solvents include, but are not limited to, aliphatic and aromatic hydrocarbons, halogenated hydrocarbons, esters, ketones, glycol ether esters, and the like. Any solvent that is stable to the reaction conditions, will not react with the carboxylic acid anhydride, and will dissolve the reactants and polymer products is suitable.

The products usually isolated from the process of the invention are ester-terminated polyethers. These materials are usually less useful than the hydroxy-terminated polymers. The ester groups can be removed by any conventional method known to those skilled in the art, including base-catalyzed transesterification or catalytic hydrogenation.

An important and unexpected advantage of the process of the invention is that tetrahydrofuran polymers having a narrow molecular weight distribution can be produced. The process overcomes the need to use costly, labor-intensive post-treatment methods, which obtain narrow distributions by distillation or solvent extraction. Of course, these techniques can still be practiced if desired with the polymers made by the process of the invention to further narrow molecular weight distribution. Since additional monomers need not be added, and since control of reaction temperature is not especially critical, the process of the invention is easier to practice than prior-art methods that rely on these techniques for obtaining poly(THF) of relatively narrow molecular weight distribution.

The following examples merely illustrate the invention. Those skilled in the art will recognize numerous variations that are within the spirit of the invention and scope of the claims.

EXAMPLE 1

Silica-alumina extrudates (Davison/Grace grade 979) are crushed to 10/30 mesh, and are dried overnight at 120° C. under vacuum. A jacketed reactor tube (2.5 cm diameter) is wet-packed in THF with the silica-alumina (55.5 g) to give a 24 cm-tall catalyst bed. The reactor is heated to 50° C., and a feed mixture of THF/acetic anhydride (15/1 mole ratio) is passed upwardly through the bed at a rate of 1 mL/min. Aliquots of the colorless product solution are periodically collected and distilled to remove unreacted THF and acetic anhydride. Each aliquot contains about a 35% yield (based on the amount of THF used) of polytetramethylene ether glycol diacetate having a number average molecular weight ($M_n$) of about 650 and a polydispersity ($M_w/M_n$) of about 1.9 (as measured by gel-permeation chromatography). Transesterification with methanol according to the method of U.S. Pat. No. 4,230,892 gives polytetramethylene ether glycol having $M_n=630$ and $M_w/M_n=2.0$.

EXAMPLE 2

A stirred reaction vessel is charged with THF (432 g), acetic anhydride (44 g), and silica-alumina catalyst (Davison/Grace grade 979 extrudates that have been crushed to 10/30 mesh and dried overnight under vacuum at 120° C.) (44 g). After heating at 50° C. for 3 h, the reaction mixture is filtered, and unreacted THF and acetic anhydride are removed by distillation. Polytetramethylene ether glycol diacetate is isolated in 55% yield. The polymer is transesterified as in Example 1 to give polytetramethylene ether glycol having $M_n=740$ and $M_w/M_n=2.2$.

COMPARATIVE EXAMPLE 3

The procedure of Example 1 is followed except that an acid-washed montmorillonite clay (Englehard F-124) is used in place of the amorphous silica-alumina catalyst. Polytetramethylene ether glycol diacetate having $M_n=700$ and $M_w/M_n=3.4$ is obtained.

COMPARATIVE EXAMPLE 4

The procedure of Example 2 is followed except that an acid-washed montmorillonite clay (Sud Chemie KO) is used in place of the amorphous silica-alumina catalyst. Polytetramethylene ether glycol diacetate having $M_n=660$ and $M_w/M_n=3.3$ is obtained.

We claim:

1. A process for producing a tetrahydrofuran polymer having a narrow molecular weight distribution, said process comprising polymerizing tetrahydrofuran in the presence of a carboxylic acid anhydride and an effective amount of an amorphous silica-alumina catalyst, wherein the amorphous silica-alumina catalyst has an $Al_2O_3$ content within the range of about 10 to about 30 weight percent, and wherein the resulting tetrahydrofuran polymer has a number average molecular weight within the range of about 200 to about 5,000, and a molecular weight distribution ($M_w/M_n$) less than about 3.

2. The process of claim 1 wherein tetrahydrofuran is copolymerized with a cationically polymerizable monomer selected from the group consisting of epoxides and oxetanes.

3. The process of claim 1 wherein the polymerization is performed at a temperature within the range of about 20° C. to about 70° C.

4. The process of claim 1 wherein the tetrahydrofuran polymer is converted to a polytetrahydrofuran diol.

5. A process for producing a tetrahydrofuran polymer having a narrow molecular weight distribution, said process comprising polymerizing tetrahydrofuran in the presence of acetic anhydride and an effective amount of an amorphous silica-alumina catalyst, wherein the amorphous silica-alumina catalyst has an $Al_2O_3$ content within the range of about 10 to about 30 weight percent, and wherein the resulting tetrahydrofuran polymer has a number average molecular weight within the range of about 200 to about 5,000, and a molecular weight distribution ($M_w/M_n$) less than about 3.

6. The process of claim 5 wherein the polymerization is performed at a temperature within the range of about 20° C. to about 70° C.

7. The process of claim 5 wherein the tetrahydrofuran polymer is converted to a polytetrahydrofuran diol.

* * * * *